United States Patent [19]

Sharkey

[11] Patent Number: 5,788,505

[45] Date of Patent: Aug. 4, 1998

[54] MEDICATION STATUS DEVICE

[76] Inventor: John J. Sharkey, 1732 Unionport Rd., Bronx, N.Y. 10462

[21] Appl. No.: 787,906

[22] Filed: Jan. 23, 1997

[51] Int. Cl.⁶ .................................................. G09B 23/28
[52] U.S. Cl. .......................... 434/262; 434/238; 206/570
[58] Field of Search ................................ 434/238, 236, 434/262, 267; 446/472, 296; 206/459.5, 570, 571, 803; 283/900

[56] References Cited

U.S. PATENT DOCUMENTS

| | | |
|---|---|---|
| D. 301,615 | 6/1989 | Vitart-Liva . |
| 3,670,435 | 6/1972 | Steward . |
| 3,999,504 | 12/1976 | Kearse . |
| 4,282,824 | 8/1981 | Lafferty . |
| 4,307,539 | 12/1981 | Klein ........................................ 446/472 |
| 4,349,338 | 9/1982 | Heppler .................................... 434/262 |
| 4,767,008 | 8/1988 | Warnecke et al. ...................... 206/570 |
| 4,817,320 | 4/1989 | Fraynd . |
| 4,905,388 | 3/1990 | Sinkow . |
| 5,031,937 | 7/1991 | Nellhaus ............................ 283/900 X |
| 5,257,940 | 11/1993 | Schaarschmidt . |
| 5,431,450 | 7/1995 | Coleman ............................ 434/238 X |

Primary Examiner—Jeffrey A. Smith
Attorney, Agent, or Firm—Leo Zucker

[57] ABSTRACT

A medication status device for reminding a person, particularly a child, to administer insulin or other medications. The device includes a display board having which a graphic image that is attractive to the person. Medication confirmation indicia on the display board indicate whether or not the medication has been administered at a certain time. Included are indicia for providing an affirmative indication to confirm administration of the medication at a certain time, and a negative indication to remind the person to administer the medication at a certain time. In one embodiment, the device also features a toy with which a child can play just before or after administering medication to himself/herself.

14 Claims, 3 Drawing Sheets

5,788,505

1

MEDICATION STATUS DEVICE

BACKGROUND OF THE INVENTION

1. Field of the Invention

The present invention relates to a device that helps persons to determine when to administer a medication, and particularly to an insulin status device for use by children.

2. Discussion of the Known Art

Medication reminder devices are generally known. For example, U.S. Pat. No. 3,999,504 (Dec. 28, 1976) shows an insulin injection reminder that maintains a record of previously used injection sites on a patient's body. The device does not act to alert a person that an injection is due at a particular time, however.

U.S. Pat. Des. No. 301,615 (Jun. 13, 1989) shows an insulin shot reminder tray, with indicia of the days of the week across a top row, and columns of three openings beneath each week day. No disclosure is provided relating to use of the tray, however. See also U.S. Pat. No. 4,282,824 (Aug. 11, 1981).

The above devices may be useful for their intended purposes, but only if a person does not forget to use them properly over a period of time. For children who must remember to take medication one or more times a day, such as diabetic children who may require both a morning and an evening administration of insulin, a need exists for a medication status device that is easy and fun to use, much like a toy. Such would ensure that the device will be used regularly, and medication that must be taken will be administered at the proper times. Preferably, the device should also confirm for the user that the medication has been taken during a most recent time period to avoid an accidental overdose. Either scenario, i.e., none or too much medication being taken during a certain time period, can have harmful results especially in the case of insulin.

SUMMARY OF THE INVENTION

An object of the invention is to provide a medication status device that is easy to use, even for a child.

Another object of the invention is to provide a medication status device that is attractive to the user, thus ensuring that the device will be used regularly.

A further object of the invention is to provide an insulin status device especially for children.

According to the invention, a medication status device comprises a display board having a feature that is attractive to a person who administers a medication at certain intervals. A medication confirmation region associated with the display board, indicates whether or not the medication has been administered at a certain time. Included are indicia for confirming an administration of the medication at a certain time, and indicia for reminding the person to administer the medication at a certain time.

For a better understanding of the invention, together with other and further objects, reference is made to the following description taken in conjunction with the accompanying drawing, and the scope of the invention will be pointed out in the appended claims.

2

Figure 3:
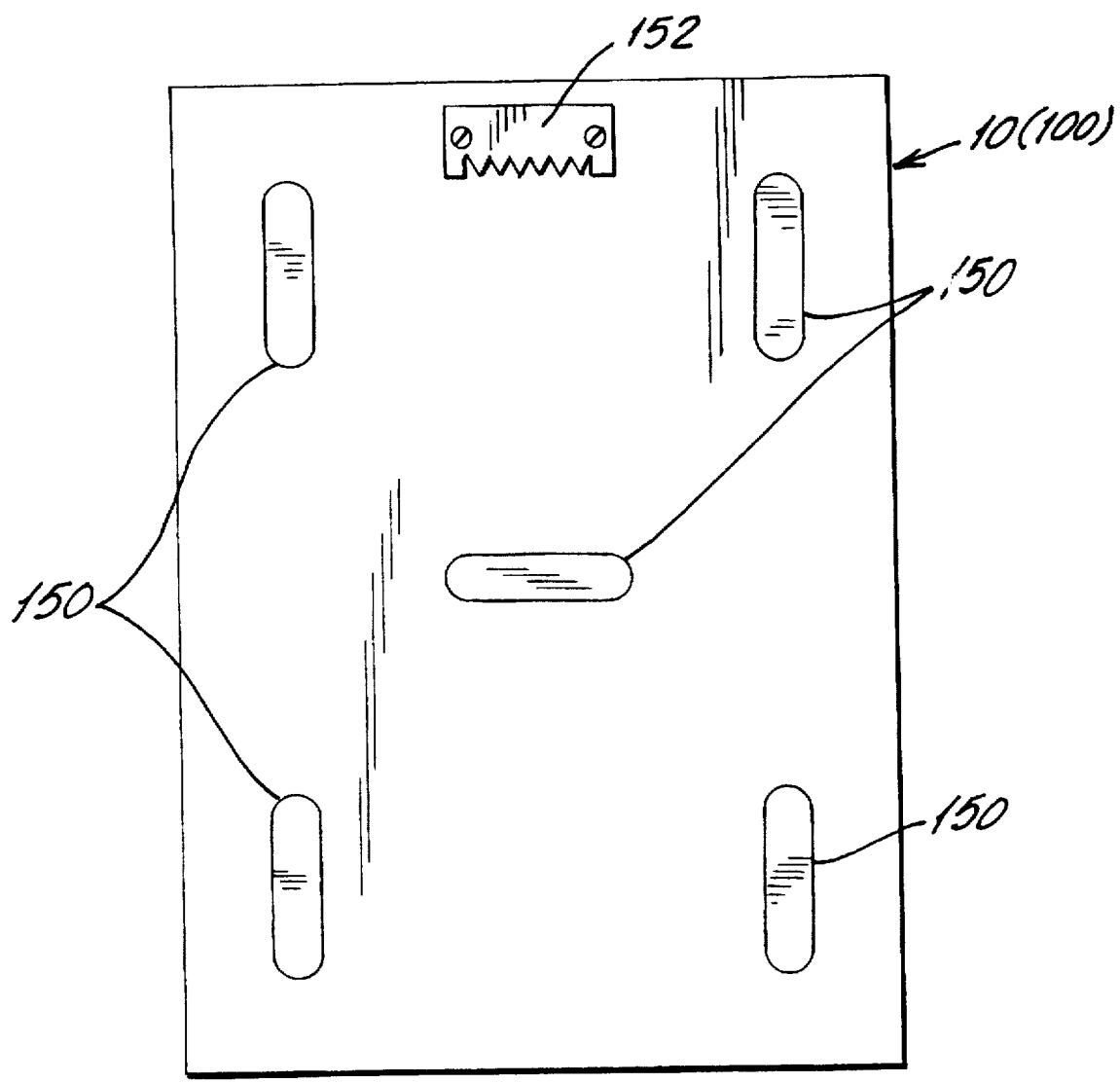

FIG. 3 is a rear view of the present device showing provisions for mounting the device.

DETAILED DESCRIPTION OF THE INVENTION

Figure 1:
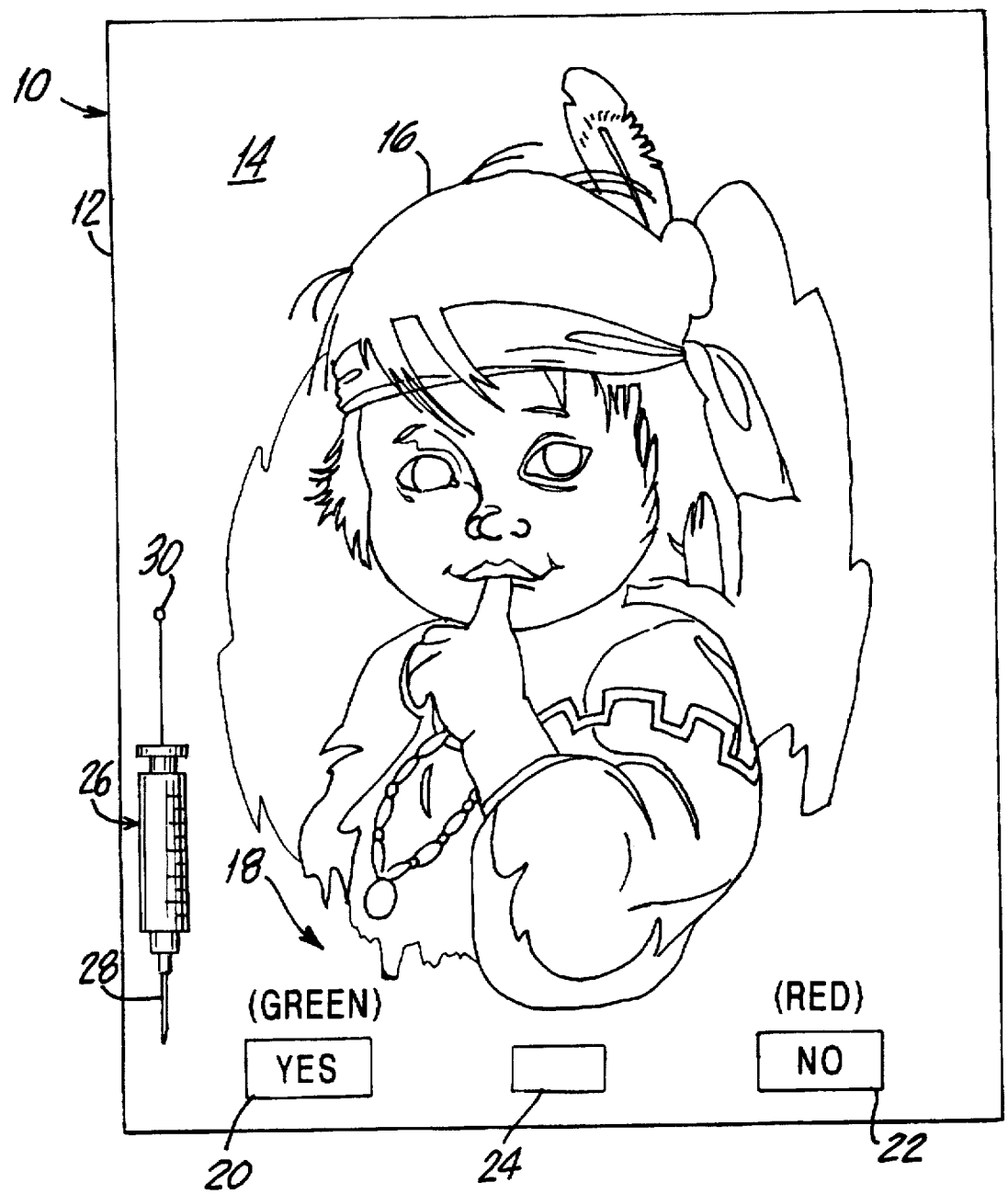
FIG. 1 is a front view of a first embodiment of a medication status device according to the invention.

FIG. 1 is a front view of a medication status device 10 according to the invention. The device 10 comprises a board 12 having a major surface 14 on which a graphic image 16 is printed or otherwise transferred. Preferably, the image 16 is one that is attractive to a person who administers a medication at certain intervals. For example, if the device 10 is used to ensure that a young boy will receive timely administrations of insulin, the image 16 may be one of an attractive child such as the young boy depicted in FIG. 1.

The mounting board 12 can be made of any rigid, durable material or laminate. Preferably, the board includes material to which a magnet will be attracted, for reasons discussed below. The major surface 14 of the board has a medication confirmation region 18 for indicating whether or not a medication has been administered at a certain time. In the embodiment of FIG. 1, the device 10 is intended for persons who receive only one administration per day, for example, a child who receives one injection of insulin upon awakening in the morning. The confirmation region 18 comprises first indicia 20 in the form of a box containing the legend "YES". Alternatively, or in addition to an affirmative word, the indicia 20 may be colored in an affirmative tone, e.g., green.

Second indicia 22 in the confirmation region 18, comprises a box containing a negative legend such as the word "NO". Alternatively, or in addition, the second indicia 22 may be colored in a negative tone, e.g., red.

After taking his or her daily insulin injection, the child uses a marker, e.g., a magnetic block piece 24 to cover or mask the second (negative) indicia 22 and leave the first (affirmative) indicia 20 exposed, thus confirming that the medication has been administered for the day. At the end of the day, before bedtime, the child moves the piece 24 to cover the affirmative indicia 20, thus leaving the negative indicia 22 exposed to remind the child to take his/her insulin when he/she awakens the following morning. During the day, if the child forgets whether or not an insulin injection was taken, he/she need only glance at the attractive display board 12 to confirm via the exposed first indicia 20 that the medication was in fact taken on time.

A toy syringe 26 having a harmless needle 28, is suspended via a string from the display board at 30. The syringe 26 attracts the attention of a child for whom the device 10 is intended, and affords the child an opportunity to interact with the device 10 in a playful manner. For example, before administering insulin to himself or herself, the child may pretend that the child of the image 16 is also a child who must receive an injection of insulin, via the toy syringe 26. That is, the child can "inject" the imaged child using the toy syringe 26, and inject himself/herself with insulin just before or after "injecting" the child of the image 16.

Figure 2:
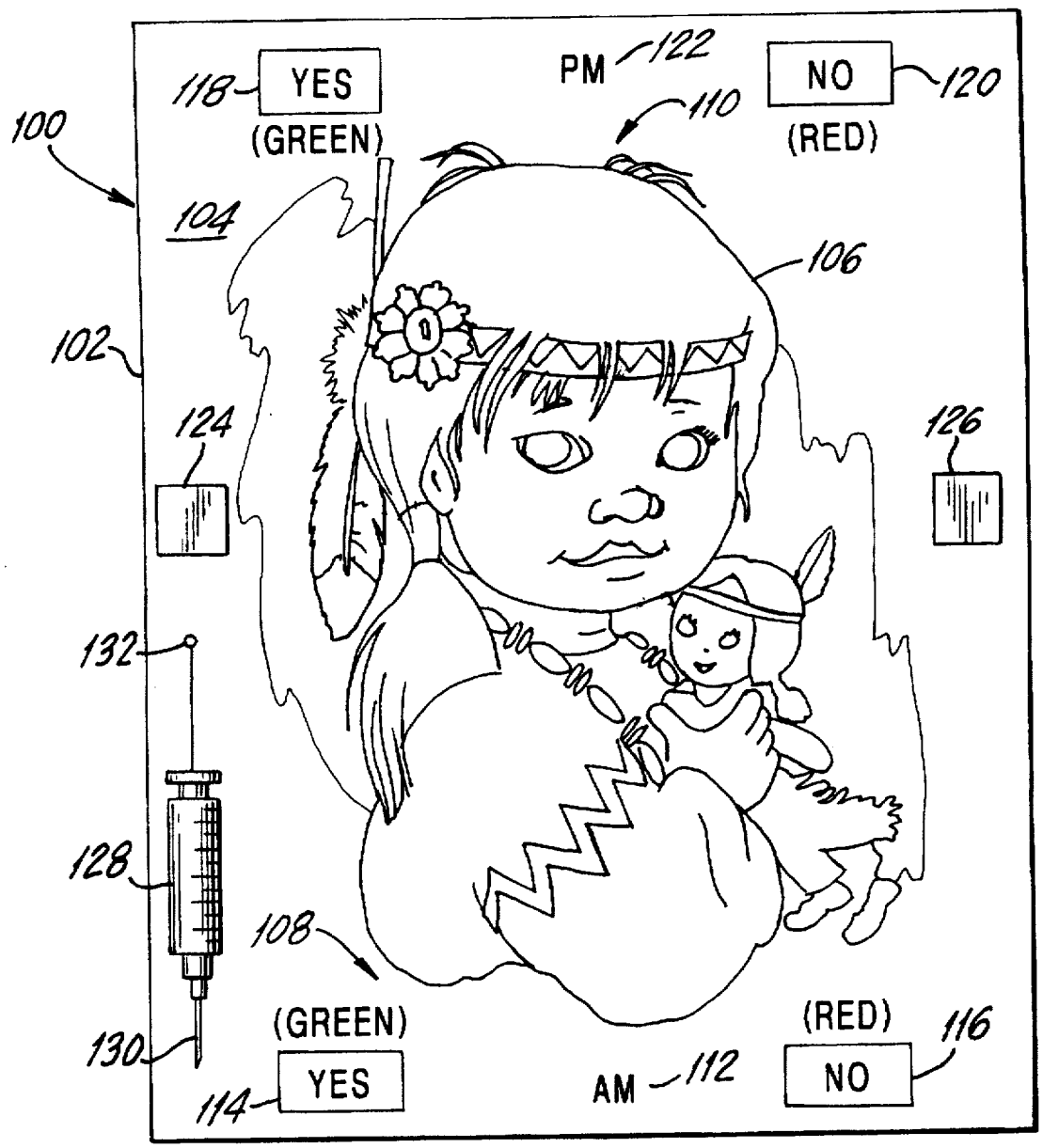
FIG. 2 is a front view of a second embodiment of a medication status device according to the invention.

FIG. 2 is a front view of a second embodiment of a medication status device 100 according to the invention. The device 100 comprises a display board 102 constructed of a rigid, durable material or laminate. Board 102 preferably also comprises material to which a magnet will be attracted.

A major surface 104 of the board 102 has a graphic image 106 printed or otherwise transferred on the surface 104. As in the embodiment of FIG. 1, the image 106 is one that is attractive to a person who administers medication at certain intervals with the aid of the present device 100. For example, if the person for whom the device 100 is intended is a young girl, the image 106 may also be that of an attractive young girl.

The device 100 in FIG. 2 is also suitable for use with persons who must take a medication more than once daily. The device 100 therefore has, for example, a morning or "AM" medication confirmation region 108 at a lower portion of the board surface 104, and an evening or "PM" medication confirmation region 110 at an upper portion of the device surface 104.

The morning confirmation region 108 is similar to the confirmation region 18 in FIG. 1, and also includes a designation 112 such as the letters "AM" to designate the region 108 accordingly. Region 108 thus includes first (affirmative) indicia 114, and second (negative) indicia 116. The indicia 114, 116 may be lettered and colored the same as the indicia 20, 22 in FIG. 1.

The evening (PM) confirmation region 110 also comprises first indicia 118 and second indicia 120 similar to the indicia 114, 116. Between the indicia 118, 120 is a designation 122, for example, the letters "PM" that identify the region 110 with respect to the time of day to which it relates.

Two markers in the form of magnetic block pieces 124, 126 are provided for placement on the indicia of the morning and the evening confirmation regions 108, 110. One of the markers is used to mask a selected one of the indicia 114, 116 of the morning confirmation region 108, and the other one of the markers is used to mask a selected one of the evening confirmation region indicia 118, 120. A toy syringe 128 having a harmless needle 130, is suspended from the device board at 132, to one side of the image 106.

The medication status device 100 is used in a similar fashion as the device 10 in FIG. 1, except that the child or other person for whom the device 100 is intended may use the device both upon awakening in the morning and later in the afternoon of the same day. For example, after taking a morning injection of insulin, a child moves the piece 124 to cover the "NO" indicia 116, thus leaving the "YES" indicia 114 exposed to confirm that his/her medication was taken in the morning or "AM" 112. After taking an afternoon injection on the same day, the child moves the piece 126 to cover the "NO" indicia 120, thus leaving the "YES" indicia 118 exposed to confirm that his/her medication was taken in the afternoon or "PM" 122. Before going to sleep that night, the child moves both pieces 124, 126 to cover both the AM and the PM "YES" indicia 114, 118, thus leaving both "NO" indicia 116, 120 exposed to remind the child to take his/her insulin when the child awakens the following day.

FIG. 3 is a rear view of the present medication status device 10 (or 100), showing provisions for mounting the device. It is preferred that the present device be capable of mounting on an enclosure in which the administered medication is stored. For example, if used to facilitate insulin administration, it is preferred that the device be mounted on the door of a refrigerator in which the insulin is stored. Because refrigerator doors will usually hold a magnet placed on them, the rear of the device 10 or 100 has a set of magnet pieces or strips 150 fixed or embedded at regular intervals on the rear surface of the display board 12 (or 102). Thus, the entire device can be placed conspicuously on a refrigerator door and held there by the action of a magnetic force. In addition, a universal hook member 152 is fixed at the top center of the rear of the device, so the device can be suspended from a wall hook or nail if desired.

While the foregoing description represents preferred embodiments of the invention, it will be obvious to those skilled in the art that various modifications can be made without departing from the true spirit and scope of the invention as pointed out in the following claims.

What I claim is:

1. A medication status device, comprising:

a display board having a configuration that is attractive to a person who administers a medication at certain intervals;

the board being constructed and arranged for mounting of the board on a supporting surface; and a medication confirmation region on said display board, for allowing a person to confirm whether or not a medication has been administered at a certain time, the confirmation region including affirmative indicia for confirming an administration of said medication at a certain time of day, negative indicia for reminding the person to administer said medication at said time of day, and a movable device for masking a selected one of the affirmative and the negative indicia.

2. A medication status device according to claim 1, wherein the display board configuration has a graphic image that is attractive to a child.

3. A medication status device according to claim 2, wherein the display board configuration includes a toy associated with the display board for attracting the attention of a child to whom the medication is administered.

4. A medication status device according to claim 3, wherein said toy comprises a toy syringe.

5. A medication status device according to claim 2, wherein said graphic image is of a child.

6. A medication status device according to claim 5, including a toy connected with the display board for attracting the attention of a child to whom the medication is administered.

7. A medication status device according to claim 6, wherein said toy comprises a toy syringe.

8. A medication status device according to claim 1, wherein the display board includes at least one mount for mounting the display board on an enclosure in which the medication is stored.

9. A medication status device according to claim 8, wherein said mount comprises a magnet for holding said board on the enclosure by a magnetic force.

10. A medication status device according to claim 1, wherein said affirmative indicia includes the word YES, and said negative indicia includes the word NO.

11. A medication status device according to claim 10, wherein the display board has a number of said medication confirmation regions each corresponding to a different time of a given day.

12. A medication status device according to claim 11, wherein one of said medication confirmation regions is designated a morning or AM region, and another one of said regions is designated an afternoon or PM region.

13. A medication status device according to claim 1, wherein said movable device comprises a block piece for masking said negative indicia when said affirmative indicia is to be exposed, and for masking said positive indicia when said negative indicia is to be exposed.

14. A medication status device according to claim 13, wherein said block piece is a magnetic block piece.

\* \* \* \* \*